United States Patent
Wahi et al.

(10) Patent No.: US 6,844,005 B2
(45) Date of Patent: Jan. 18, 2005

(54) ELECTROSTATICALLY CHARGED NASAL APPLICATION PRODUCT WITH INCREASED STRENGTH

(75) Inventors: Ashok L. Wahi, Hillsborough, NJ (US); Kenneth Sugathan, Franklin Park, NJ (US)

(73) Assignee: Trutek Corp, Hillsborough, NJ (US)

( * ) Notice: Subject to any disclaimer, the term of this patent is extended or adjusted under 35 U.S.C. 154(b) by 370 days.

(21) Appl. No.: 10/082,978

(22) Filed: Feb. 25, 2002

(65) Prior Publication Data

US 2003/0161790 A1 Aug. 28, 2003

(51) Int. Cl.[7] .............. A61F 13/02; A61K 9/14
(52) U.S. Cl. ............. 424/434; 424/443; 424/484; 424/485; 424/486
(58) Field of Search .............. 424/434, 443, 424/484, 485, 486, 43

(56) References Cited

U.S. PATENT DOCUMENTS 5,468,488 A * 11/1995 Wahi .............. 424/78.03
5,674,481 A * 10/1997 Wahi .............. 424/78.03

* cited by examiner

Primary Examiner—Carlos A. Azpuru
(74) Attorney, Agent, or Firm—Kenneth P. Glynn, Esq.

(57) ABSTRACT

The present invention relates to a nasal topical application product for restricting the flow of airborne contaminants into a human nasal passage by creation of a proximate, enhanced electrostatic field. This nasal application product includes: (a) a plurality of masses of one or more electrostatic polymers; and, (b) a topical carrier having the plurality of masses dispersed through a portion thereof. At least one of the electrostatic polymers is a poly (dimethyl diallyl ammonium chloride) polymer and is included in the product in an amount of at least 10% by weight, based on the total weight of the polymers and the topical carrier. The nasal application product may be topical solutions, semisolids, spray solutions and vaporizable solutions. Topical applications may be in the form of ointments, pastes, creams and gels. The carrier of the nasal application product of the present invention may be selected from the group consisting of dilutents, volatile spray carriers, lotions, solvents, gels and hydrogels. In some embodiments, substrates, e.g., bandage type substrates, with adhesive on one side and the product polymer(s) and carrier on the opposite side, may be employed.

20 Claims, 2 Drawing Sheets

ELECTROSTATIC MATERIAL CREATING FIELD
IN AREA OF NASAL PASSAGES

1.) SOLID-FLEXIBLE, SEMIRIGID, RIGID
2.) FOAM-FLEXIBLE, SEMIRIGID, RIGID
3.) SEMISOLID, GEL, HYDROGEL
4.) SOLUTION-OINTMENT, CREAM, PASTE, SOL
(A) WITH OR WITHOUT CARRIER
(B) WITH OR WITHOUT SUBSTRATE
(C) WITH OR WITHOUT ADHESIVE

FIG. 1

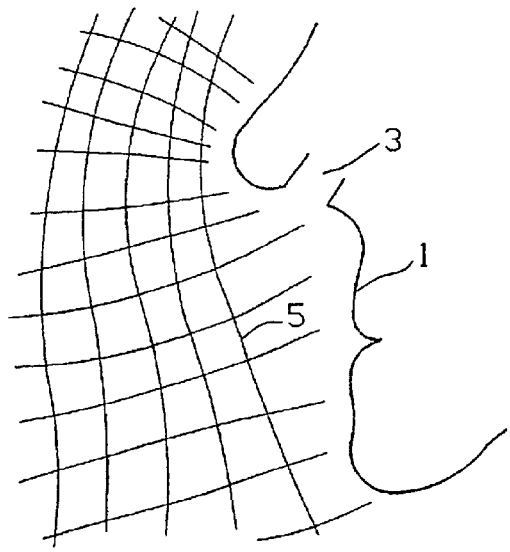
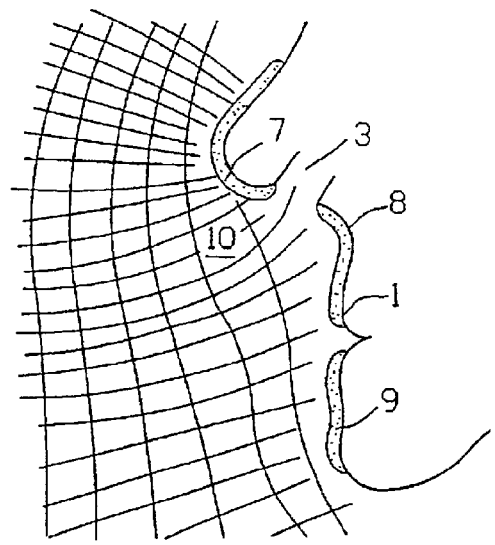
FIG. 2
FIG. 3
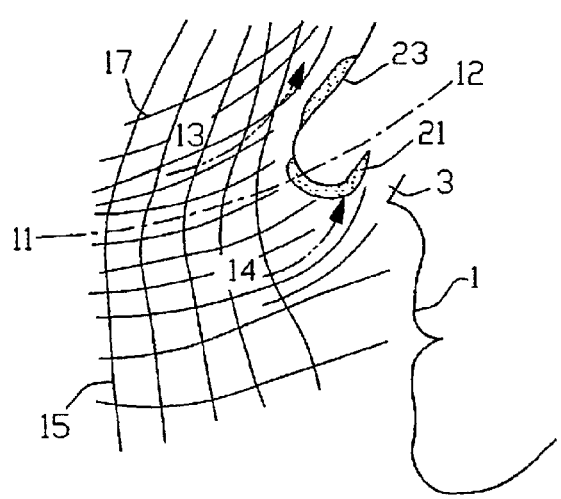
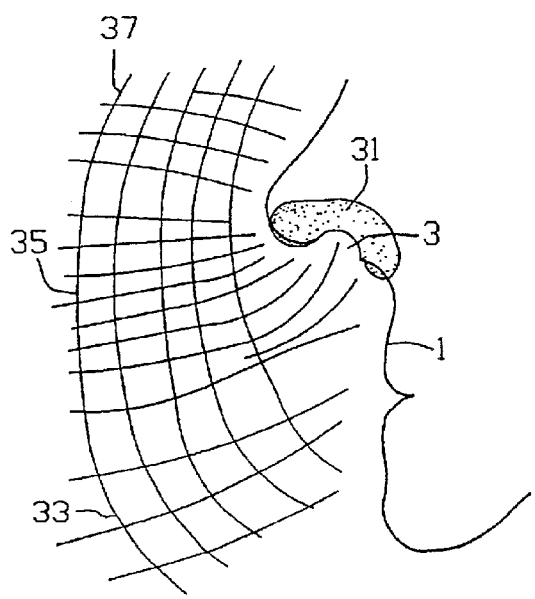
FIG. 4
FIG. 5

ELECTROSTATICALLY CHARGED NASAL APPLICATION PRODUCT WITH INCREASED STRENGTH

REFERENCE TO RELATED CASES

The present invention relates to electrostatically charged topical nasal application products which have been developed and improved since their original development as set forth in two previously issued United States patents. For this reason, the entire specification and claims are incorporated herein in their entirety by reference, as to U.S. Pat. No. 5,468,488, entitled "ELECTROSTATICALLY CHARGED NASAL APPLICATION PRODUCT AND METHOD" issued to Ashok L. Wahi, inventor, on Nov. 21, 1995, and U.S. Pat. No. 5,674,481, entitled "ELECTROSTATICALLY CHARGED NASAL APPLICATION PRODUCT" ISSUED TO Ashok L. Wahi on Oct. 7, 1997.

BACKGROUND OF THE INVENTION

1. Field of the Invention

The present invention relates to products for restricting the flow of airborne contaminants into a nasal passage by creating an electrostatic field of increased charge in an area about the nasal passage. This prevents or reduces the inflow of airborne contaminants to the nasal passage.

2. Information Disclosure Statement

U.S. Pat. No. 5,468,488 describes a method for restricting the flow of airborne contaminants into a nasal passage. It involves creating an electrostatic field in an area near a human nasal passage. The electrostatic field may either repel or attract airborne contaminants or both. The method involves applying a topical application having a plurality of masses of one or more electrostatic materials, and a carrier having the plurality of masses dispersed therein. The masses have an average cross sectional area of about one square millimeter to about 50,000 square millimeters, and are of sufficient charge to create an electrostatic field which will prevent at least some airborne contaminants from passing into a human nasal passage. The topical application may be in the form of a solution, a semisolid, a solid, a spray solution or a vaporizable solution.

U.S. Pat. No. 5,674,481 describes a product and method for restricting the flow of airborne contaminants into a nasal passage. It involves creating an electrostatic field in an area near a nasal passage. The electrostatic field may either repel or attract airborne contaminants or both. The product may take the form of a plurality of masses of one or more electrostatic materials, the masses have an average cross sectional area of about one square millimeter to about 50,000 square millimeters, the mass being of sufficient charge to create an electrostatic field which will prevent at least some airborne contaminants from passing into a nasal passage. There is also a carrier material with the plurality of masses dispersed therein. The product may be a topical solution, a semi solid, a solid, a spray solution or a vaporizable solution. Alternatively, it may be in a form which includes a substance for the carrier and, in one preferred embodiment, the substrate would be an adhesive material such as a bandage.

The aforesaid references describe various methods and products for restricting airborne contaminant flow to the nasal passage area utilizing the suggested formulae described therein. It has now been discovered that utilization of at least 10% of one specific active electrostatically charged polymer provides significantly increased charge density and efficacy as compared to other electrostatic polymers at lower, the same or higher concentrations than the present invention levels of the poly (dimethyl diallyl ammonium chloride). For this reason, notwithstanding the prior art, the present invention is neither taught nor rendered obvious thereby.

SUMMARY OF THE INVENTION

The present invention relates to a nasal topical application product for restricting the flow of airborne contaminants into a human nasal passage by creation of an artificial electrostatic field near the human nose This nasal application product includes: (a) a plurality of masses of one or more electrostatic polymers; and, (b) a topical carrier having the plurality of masses dispersed through a portion thereof. In the present invention, at least one of the electrostatic polymers is a poly (dimethyl diallyl ammonium chloride) polymer and is included in the product in an amount of at least 10% by weight, based on the total weight of the plurality of masses of one or more electrostatic polymers and the topical carrier.

The nasal application product of the present invention may be selected from the group consisting of topical solutions, semisolids, spray solutions and vaporizable solutions. Topical applications may be in the form of ointments, pastes, creams and gels.

The carrier of the nasal application product of the present invention may be selected from the group consisting of diluents, volatile spray carriers, lotions, solvents, gels and hydrogels. When the carrier is a dilutent, it may be selected from the group consisting of glycols, glycerines, organic surfactants, esters being of unsaturated fatty acids, and mixture thereof. When the carrier is a volatile spray carrier, it may be selected from the group consisting of water, natural oils, glycols, organic surfactants and mixtures thereof. When the carrier is a lotion, it may be selected from the group consisting of polyethylene glycols, natural oils, silicones, homogenizers, and mixtures thereof. When the carrier is a gel, it may be selected from the group consisting of three dimensional polymeric matrices of natural polymers, synthetic polymers, copolymers, and mixtures thereof In some preferred embodiments of the nasal application product of the present invention, the carrier includes at least one homogenizer and at least one glycol polymer.

In preferred some embodiments of the present invention nasal application product, the carrier includes about 1 to about 5% by weight of a glycol compound and about 60 to 85% by weight of water, based on the total weight of the plurality of masses of one or more electrostatic polymers and the topical carrier. Preferred nasal application product topical carrier formulae include:

(a) about 1% to about 5% by weight of a glycol compound selected from the group consisting of polyethylene glycol, polypropylene glycol and mixtures thereof;

(b) about 60% to about 85% by weight of water; and, (c) about 0% to about 2.5% of one or more stearate compounds;

all of the above weight percentages being based on the total weight of the plurality of masses of one or more electrostatic polymers and the topical carrier.

The present invention nasal application products may further include a substrate containing the topical carrier with a plurality of masses of one or more electrostatic polymers dispersed through at least a portion thereof. The substrate may be a flexible substrate, such as a cloth or other woven material or a synthetic sheet material with an adhesive thereon, e.g., a bandage type of substrate.

BRIEF DESCRIPTION OF THE DRAWINGS

The present invention should be more fully understood when the specification herein is taken in conjunction with the drawings appended hereto wherein:

FIG. 1 shows a schematically the product concept of the present invention;

FIG. 2 shows a side partial stylized view of a human illustrating a typical electrostatic field around a human nasal passage;

FIG. 3 shows the same stylized human outline as in FIG. 2 but with an artificially created electrostatic field near a persons nose to restrict the flow of airborne contaminants into the nasal passages;

FIG. 4 shows another alternative present invention embodiment wherein a combination of artificially created electrostatic fields are shown; and, FIG. 5 shows a mild artificially created electrostatic field.

DETAILED DESCRIPTION OF THE PRESENT INVENTION

The FIGS. 1 through 5 are briefly described above and are identical to the drawings set forth in the two issued patents incorporated by reference stated above. As such, the detailed explanation and description set forth therein is incorporated herein and, thus, not unnecessarily repeated here.

The present invention is based on the surprising and unexpected discovery that a significant increase in electrostatic charge density is achieved with the present invention by use of at least 10% by weight of poly (dimethyl diallyl ammonium chloride). This is contrary to experiences of the inventors wherein increase in the active (electrostatic polymer) after a level achieved at less than 8% or so, did not significantly increase the electrostatic charge density. However, in the case of the present invention, a charge density increase of about 20% to 25% was realized.

The following examples are representative of the present invention:

EXAMPLE #1

| Ingredient | % age composition by weight |
| --- | --- |
| 1. Deionized Water | 75.9 |
| 2. Potassium Sorbate | 0.1 |
| 3. Celquat SC 240 C | 3.9 |
| 4. Polawax 5% in water | 4.9 |
| 5. Agequat 400 | 12.9 |
| 6. Arlacel 165 | 1.0 |
| 7. Tween 60 | 0.1 |
| 8. Propylene Glycol | 1.2 |
| | 100.0 |

EXAMPLE #2

| Ingredient | % age composition |
| --- | --- |
| 1. Deionized water | 73.5 |
| 2. Celquat SC 240 C | 3.8 |

-continued

| Ingredient | % age composition |
| --- | --- |
| 3. Agequat 400 | 12.6 |
| 4. Polawax 5% in water | 9.5 |
| 5. Potassium Sorbate | 0.1 |
| 6. Necon LO | 0.5 |
| | 100.0 |

EXAMPLE #3

| | |
| --- | --- |
| 1. Deionized water | 84.9 |
| 2. Celquat SC 240 C | 4.0 |
| 3. Agequat 400 | 11.0 |
| 4. Potassium Sorbate | 0.1 |
| | 100.0 |

Generic/Chemical name of the above ingredients are:
Celquat SC 240 C; Quarternary Cellulosic Derivative
Polawax; Fatty Alcohol, Polysorbate Blend
Agequat 400; Poly(Dimethyl Diallyl Ammonium Chloride)
Arlacel 165; Glycerol Monostearate and Polyethylene Stearate
Necon LO; A surfactant
Tween 60; Polysorbate
Propylene Glycol; 1,2-Propane Diol Celquat SC 240C is a polyquatermary animonium cellulose manufac ed by National Starch and Chemical Company (New Jersey). Necon LO is dimethy lauramine oleate manufactured by Aizo Inc. (A New Jersey Corporation). Arlacel 165 is a 50/50 mixture of glyscerol monosterate and polyoxyethylene stearate manufactured by Uniqema Corp.

Brief Process of Formulation:

In all of the above Examples, the ingredients are added one by one, at room temperature, in the order listed to water, while stirring. No new ingredient is added until the one added before was dispersed completely. Polawax and Arlacel were dispersed by warming the mixture, to 60 degrees C., over a water bath. After all the ingredients were added, the contents were mixed well for uniformity, let cool to room temperature and bottled.

EXAMPLE #4

| Ingredient | Weight (Kg/15 Kg) | % w/w |
| --- | --- | --- |
| 1. Polawax (5% dispersion) | 0.7500 | 5.00 |
| 2. Propylene Glycol | 0.3000 | 2.00 |
| 3. Celquat SC-240C | 0.6000 | 4.00 |
| 4. Agequat 400 | 1.6500 | 11.00 |
| 5. Methylparaben | 0.0300 | 0.20 |
| 6. Propylparaben | 0.0150 | 0.10 |
| 7. Tetrasodium Edetate | 0.0075 | 0.05 |
| 8. Arlacel 165 | 0.1500 | 1.00 |
| 9. Tween 60 | 0.0150 | 0.10 |
| 10. Gerinall-II | 0.0450 | 0.30 |
| 11. Water | 11.4375 | 76.25 |
| TOTAL | 15.0000 | 100.00 |

Prodedure:

In a suitable container prepare a 5% dispersion of Polawax in water by mixing 37.5 g in 750 g of water previously heated at 70 plus of minus 5 degrees C. (Step A)

In a tared stainless steel container with 10 Kg of water previously heated at 70 plus of minus 5 degree C. and stirred mechanically, add Celquat SC-240C gradually, directly into the vortex. Make sure no clumps are formed. As the dispersion thickens, increase the speed of the mixer enough to maintain the movement of the surface and the bulk of the dispersion. Allow mixing for one to one and a half hour to get a clear, uniform, transparent dispersion at 70 degrees C. Add sequentially Tetrasodium Edetate, Arlacel 165, Tween 60 and Agequat 400 with mixing, making sure that each ingredient is completely dissolved or dispersed before adding the next one. (Step B)

Add dispersion in step A to the dispersion in step B with continued mixing. Allow the mixture to cool down gradually to about 50 degrees C. (Step C)

In a suitable container dissolve Methylparaben, Propylparaben and Germall-II in Propylene Glycol and heat. (Step D)

When the temperature of the mixture from step D reaches 50 degrees C. add solution in step C with continued mixing. (Step E)

Dilute the combined mixture from step E to 15.0 Kg by adding Water previously heated at 50 degrees C. and continue mixing.

Allow the product to cool to 30 degrees C. to form a gel.

Transfer the bulk gel to suitable polyethylene lined containers.

Comparative tests of electrostatic charge density revealed an increase of 20% to 25% as compared to prior art formulations and as compared to other formulations having over 10% electrostatic polymer using actives other than poly (dimethyl diallyl ammonium chloride).

Obviously, numerous modifications and variations of the present invention are possible in light of the above suggestions. It is therefore understood that within the scope of the appended claims, the invention may be practiced otherwise than as specifically described herein.

What is claimed is:

1. A nasal topical application product for restricting the flow of airborne contaminants into a human nasal passage by creation of an artificial electrostatic field near the human nose, wherein the nasal application product consists essentially of:
    (a) a plurality of masses of one or more electrostatic polymers; and,
    (b) a topical carrier having said plurality of masses dispersed through a portion thereof;
wherein at least one of said one or more electrostatic polymers is a poly (dimethyl diallyl ammonium chloride) polymer and is included in said product in an amount of at least 10% by weight, based on the total weight of said plurality of masses of one or more electrostatic polymers and said topical carrier.

2. The nasal application product of claim 1 wherein said product is selected from the group consisting of topical solutions, semisolids, spray solutions and vaporizable solutions.

3. The nasal application product of claim 1 wherein said product is selected from the group consisting of ointments, pastes, creams and gels.

4. The nasal application product of claim 1 wherein said carrier is selected from the group consisting of diluents, volatile spray carriers, lotions, solvents, gels and hydrogels.

5. The nasal application product of claim 1 wherein said carrier is a dilutent selected from the group consisting of alcohols, glycerines, organic surfactants, esters being of unsaturated fatty acids, and mixture thereof.

6. The nasal application product of claim 4 wherein said carrier is a volatile spray carrier selected from the group consisting of water, natural oils, glycols, organic surfactants and mixtures thereof.

7. The nasal application product of claim 4 wherein said carrier is a lotion selected from the group consisting of polyethylene glycols, natural oils, silicones, homogenizers, and mixtures thereof.

8. The nasal application product of claim 4 wherein said carrier is a gel selected from the group consisting of three dimensional polymeric matrices of natural polymers, synthetic polymers, copolymers, and mixtures thereof.

9. The nasal application product of claim 1 wherein said carrier includes at least one honogenizer and at least one glycol polymer.

10. The nasal application product of claim 9 wherein said carrier includes about 1 to about 5% by weight of a glycol compound and about 60 to 85% by weight of water, based on the total weight of said plurality of masses of one or more electrostatic polymers and said topical carrier.

11. The nasal application product of claim 10 wherein said topical carrier includes:
    (a.) about 1% to about 5% by weight of a glycol compound selected from the group consisting of polyethylene glycol, polypropylene glycol and mixtures thereof;
    (b.) about 60% to about 85% by weight of water; and,
    (c.) about 0% to about 2.5% of one or more stearate compounds;
    all of the above weight percentages being based on the total weight of said plurality of masses of one or more electrostatic polymers and said topical carrier.

12. The nasal application product of claim 1 wherein said product further includes a substrate containing said carrier with said plurality of masses of one or more electrostatic polymers dispersed through a portion thereof.

13. The nasal application product of claim 11 wherein said substrate is a flexible substrate having an adhesive thereof.

14. The nasal application product of claim 11 wherein said substrate is a bandage.

15. The nasal application product of claim 12 wherein the nasal application product of claim 1 wherein said carrier includes at least one homogenizer and at least one glycol polymer.

16. The nasal application product of claim 15 wherein the nasal application product of claim 9 wherein said carrier includes about 1 to about 5% by weight of a glycol compound and about 60 to 85% by weight of water, based on the total weight of said plurality of masses of one or more electrostatic polymers and said topical carrier.

17. The nasal application product of claim 16 wherein said topical carrier includes:
    a. about 1% to about 5% by weight of a glycol compound selected from the group consisting of polyethylene glycol, polypropylene glycol and mixtures thereof;
    b. about 60% to about 85% by weight of water; and,
    c. about 0% to about 2.5% of one or more stearate compounds;
    all of the above weight percentages being based on the total weight of said plurality of masses of one or more electrostatic polymers and said topical carrier.

18. The nasal application product of claim 13 wherein said carrier includes at least one homogenizer and at least one glycol polymer.

19. The nasal application product of claim 18 wherein said carrier includes about 60 to 85% by weight of water, based on the total weight of said plurality of masses of one or more electrostatic polymers and said topical carrier.

20. The nasal application product of claim 19 wherein said topical carrier includes:
 a. about 1% to about 5% by weight of a glycol compound selected from the group consisting of polyethylene glycol, polypropylene glycol and mixtures thereof;
 b. about 60% to about 85% by weight of water; and,
 c. about 0% to about 2.5% of one or more stearate compounds;
 all of the above weight percentages being based on the total weight of said plurality of masses of one or more electrostatic polymers and said topical carrier.

* * * * *